United States Patent [19]

Barney

[11] Patent Number: 4,909,065

[45] Date of Patent: Mar. 20, 1990

[54] CONTAINED RADIOLOGICAL ANALYTICAL CHEMISTRY MODULE

[75] Inventor: David M. Barney, Scotia, N.Y.

[73] Assignee: The United States of America as represented by the United States Department of Energy, Washington, D.C.

[21] Appl. No.: 337,982

[22] Filed: Apr. 14, 1989

Related U.S. Application Data

[62] Division of Ser. No. 127,311, Dec. 2, 1987, Pat. No. 4,838,098.

[51] Int. Cl.$^4$ ............................................. G01N 7/00
[52] U.S. Cl. ........................................ 73/19; 73/61 R
[58] Field of Search ................ 73/19, 26, 27, 61 R, 73/61.1 R, 863.71, 864.81; 55/55, 189; 422/83, 98

[56] References Cited

U.S. PATENT DOCUMENTS

| | | | |
|---|---|---|---|
| 3,673,853 | 7/1972 | Griswold et al. | 73/19 |
| 4,289,018 | 9/1981 | Hellouin De Menibus | 73/19 |
| 4,319,479 | 3/1982 | Iwamura et al. | 73/19 |
| 4,713,772 | 12/1987 | Carlson | 73/863.31 |
| 4,745,795 | 5/1988 | Emmert | 73/19 |

*Primary Examiner*—Hezron E. Williams

*Attorney, Agent, or Firm*—William W. Randolph; William R. Moser; Richard E. Constant

[57] ABSTRACT

A system which provides analytical determination of a plurality of water chemistry parameters with respect to water samples subject to radiological contamination. The system includes a water sample analyzer disposed within a containment and comprising a sampling section for providing predetermined volumes of samples for analysis; a flow control section for controlling the flow through the system; and a gas analysis section for analyzing samples provided by the sampling system. The sampling section includes a controllable multiple port valve for, in one position, metering out sample of a predetermined volume and for, in a second position, delivering the material sample for analysis. The flow control section includes a regulator valve for reducing the pressure in a portion of the system to provide a low pressure region, and measurement devices located in the low pressure region for measuring sample parameters such as pH and conductivity, at low pressure. The gas analysis section which is of independent utility provides for isolating a small water sample and extracting the dissolved gases therefrom into a small expansion volume wherein the gas pressure and thermoconductivity of the extracted gas are measured.

9 Claims, 2 Drawing Sheets

CONTAINED RADIOLOGICAL ANALYTICAL CHEMISTRY MODULE

This is a division of application Ser. No. 127,311 filed Dec. 2, 1987 now U.S. Pat. No. 4,838,098.

FIELD OF THE INVENTION

The present invention relates to a unit for enabling measurement of water chemistry properties of a radiological sample, the unit or module preferably being a modification of a conventional radiological glove box. The invention also relates an improved dissolved gas analyzer for use in radiological environments as part of the main unit or module, or independently thereof.

BACKGROUND OF THE INVENTION

The chemical analysis of radioactive water presents obvious problems because of the danger of contamination of personnel and equipment. In view of this danger it is desirable to keep the amount of sample handling to a minimum and to carry out the testing and measuring as rapidly as possible. In general, previous analysis methods used in, for example, dissolved gas measurement, have involved commercially available gas chromatography equipment using relatively large (approximately 1 liter) samples of water with a high possibility of radiological contamination.

As noted above, one object of the present invention involves a modification of a standard radiological glovebox. Some examples of gloveboxes and like devices of possible interest include those disclosed in U.S. Pat. Nos. 2,786,740 (Taylor et al); 2,862,307 (Bloomer et al); 3,536,370 (Evans et al); 3,888,556 (Strange et al); 3,907,389 (Cox et al); and 4,108,509 (Piet et al).

As was also noted above, a further aspect of the invention concerns apparatus for measuring dissolved gases in radioactive water. The prior art in this general field includes U.S. Pat. Nos. 2,146,300 (Keeler); 3,673,853 (Griswald et al); 4,184,359 (Gracey); 4,288,062 (Gupta et al); and 4,289,018 (Hellorin de Menibus). Briefly considering these patents, the Griswald et al patent discloses a method and apparatus for measuring carbon dioxide wherein a pump is used to withdraw a sample to passageway for analysis using diffusion techniques. The Gracey patent discloses a gas monitor for a liquid flow line including a chamber for separating dissolved gases out of water using a pressure drop. The Hellorin de Menibus patent discloses a method and apparatus for removing dissolved gases from a liquid, using a system including a tank and a vacuum pump, wherein a vacuum is applied to the liquid to desolubilize the gases. The Gupta et al patent discloses an apparatus for monitoring the carbon content of the atmosphere in a furnace which utilizes selective absorption of infrared radiation. The Keeler patent discloses a gas analysis apparatus wherein the thermal conductivity of the gas is determined.

SUMMARY OF THE INVENTION

In accordance with one aspect of the invention, a system or unit is provided, which preferably takes the form of a modification of a standard radiological laboratory glovebox enclosure, for enabling the analytical determination of a plurality of water chemistry parameters. These parameters include, for example, pH, conductivity, suspended solids, dissolved hydrogen, carbon dioxide and total gas. The unit also permits the aliquoting and dilution of liquid samples and the performance of titrametric analysis. The unit of the invention is basically a microanalytical system for performing analysis of this type in a radiologically safe manner in a glovebox enclosure, such that all operations can be performed within easy reach of the attached gloves. All electrical and reagent feed connectors are located outside of the containment or enclosure using strip or bulkhead connectors, thereby simplifying servicing of the unit as well as facilitating storage or shipment.

The unit includes a number of features which reduce the amount of sample handling and provide other important advantages over the prior art. In this regard, the unit is typically installed in a pressurized system, with a pressure reducer-flow control means being provided to permit the high pressure tubing used to reach system pressure, thereby eliminating the formation of gas bubbles in the lines. A low pressure region is provided wherein pH and conductivity are measured, with the necessary pressure drop being provided by a first pressure regulator. A small bore tubing coil, sized to provide the desired flowrate, creates a pressure drop that is amplified as a function of flowrate. A second, back pressure regulator contains the liquid flow and enables discharge thereof to atmospheric pressure. The tubing coil is shielded to reduce radiation levels and preferably accommodates a radiation detector for monitoring the liquid radiation levels.

The unit also employs sampling loops and six port valves to minimize the amount of liquid that is handled, thereby reducing radiation exposure and waste handling. The system of the invention is an "on line" system which reduces the potential for spills and also reduces exposure to radiation by operating personnel. The system also greatly reduces analysis time (typically to less than 15 minutes from the time the sample is introduced into the system).

As mentioned above, a further aspect of the invention concerns the provision of gas analyzer apparatus for use in radiological environments in a radiologically safe manner which has special utility in the chemical analysis unit or module described above but which also has general utility. The gas analysis apparatus of the invention is miniaturized and in an embodiment of general utility, provides for extraction of a small sample of water from the process stream (e.g. about 15 cc) in a short length of tubing isolated by a pair of valves. This sample is transferred into a radiological containment (such as that described previously), preferably through a set of double doors, for connection to the analysis equipment.

The dissolved gas measurement apparatus of the invention includes a pressure sensor preferably in the form of a capacitance manometer for measuring total pressure, and a thermal conductivity bridge for measuring the hydrogen concentration in an expanded gas sample. Infrared detectors, specifically adapted to the specific gas measured, are used to determine the concentration of gases such as carbon dioxide.

Other features and advantages of the invention in both its aspects will be set forth in, or apparent from, the description of preferred embodiments thereof which follows.

DESCRIPTION OF THE PREFERRED EMBODIMENTS

Figure 1:
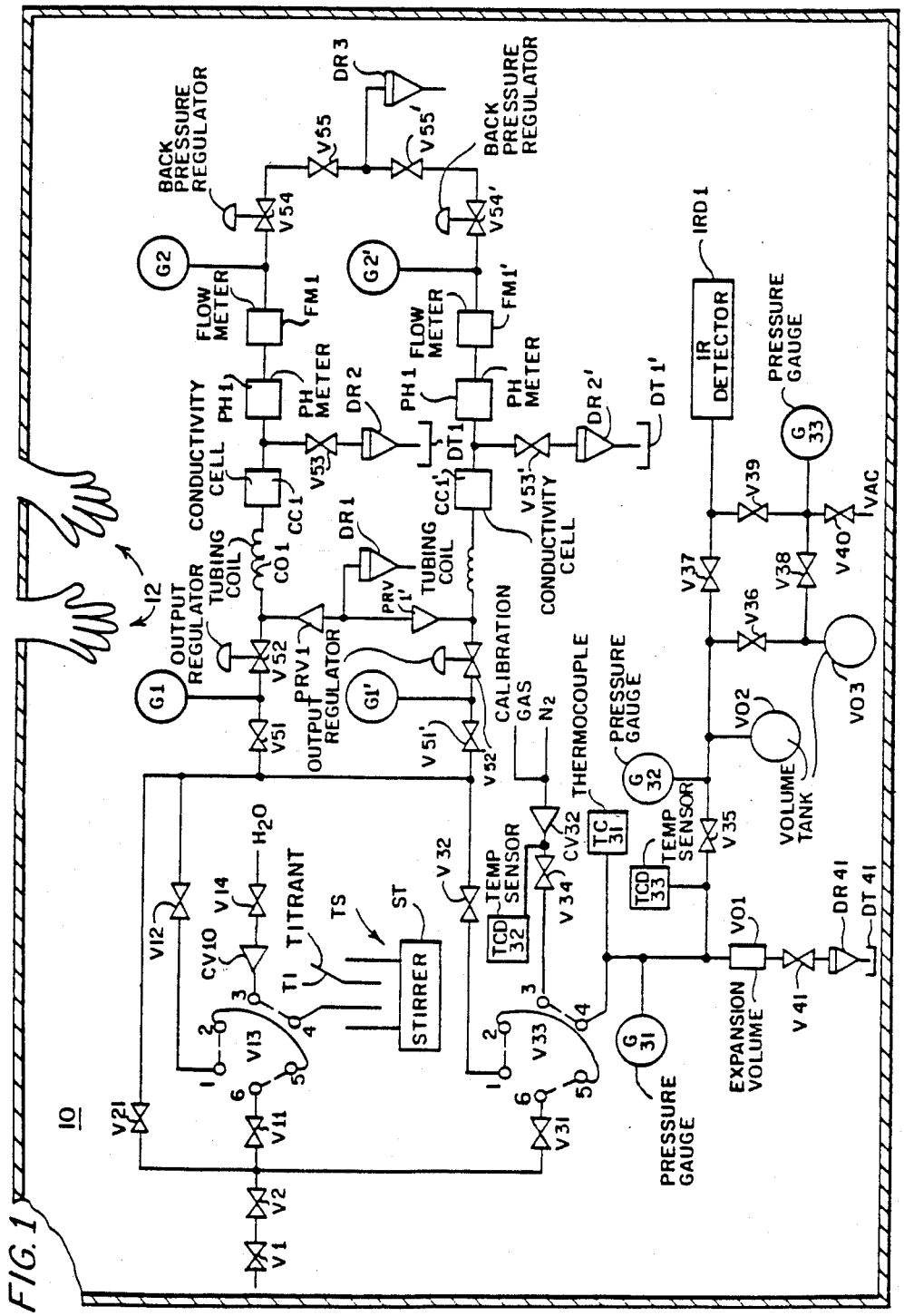
FIG. 1 is a schematic diagram of the chemical analysis unit of the invention.

Referring to FIG. 1, the basic in-line contained radiological analytical system or module of the invention is shown. The system is contained within a glovebox or like containment, indicated schematically at 10 and including gloves indicated at 12 and is adapted to provide the analytical determination of a number of water chemistry parameters such as pH, conductivity, suspended solids, and dissolved hydrogen, carbon dioxide and total gas.

The basic system is divided into three parts or sections, a sampling section used to obtain predetermined volumes of samples for analysis at system pressures, a flow control section used to control the flow through the total system, and a dissolved gas analysis section.

The sampling section itself will be considered and is itself divided into three parts. The sample input to the system includes inlet globe valves V1 and V2, and a sample for titration is obtained at a six-port valve V13 by passing the sample flow through a further globe valve V11 and the six-port valve V13, while a water inlet is connected to valve V13 through a globe valve V14 and a check valve CV10. The path from ports 2 and 5 of valve V13 provides a predetermined loop volume. When valve V13 is rotated through one-sixth of a turn, this volume is connected across the ports 3 and 4. The sample is flushed from the loop and is then analyzed by a titration system indicated at TS and including a stirrer ST and titrant inlet TI, using standard titrimetric procedures. The stirrer ST can, for example, be a Fisher Stirrer Model 460 which is part of the Fisher Computer-Aided Titrimeter.

The flow control section comprises a pair of redundant branches; the components of each branch are the same and the components of the second branch have been given the same reference numerals and/or letters as the first branch but with a prime attached. This redundancy allows repairs without affecting the overall operation of the system. Considering the first (upper) branch as typical, this branch includes an inlet globe valve V51, a first gauge G1, an output pressure regulator valve V52 (which provides regulation to approximately 100 psi), a tubing coil CO1, a conductivity cell CC1, a pH meter PH1, a flow meter FM1, a further gauge G2, a back pressure regulator V54 (which also provides regulation to about 100 psi) and a further globe valve V55. The junction between output regulator valve V52 and tubing coil CO1 is connected to a common drain or bottle DR1 through a pressure relief valve PRV1, and the junction between conductivity cell CC1 and meter PH1 is connected through a globe valve V53 to a corresponding individual drain bottle DR2 and an associated drain tray DT1. As illustrated, the junction between valves V55 and V55' is conected to a further drain or bottle DR3.

It is noted that the reduction in pressure provided at valve V52 (and valve V52') permits the use of simpler forms of conductivity cell CC1 (and CC1'), pH meter PH1 (and PH1') and flow meter FM1 (and FM1') than is required for high pressure operations. Further, the flow control section of the system of FIG. 1 utilizes the output regulator valve V52 (and V52') to supply a constant pressure to tubing coil CO1 (and CO1'). The back pressure regulator valve V54 (and V54') is used to control the flow through the system. This regulation is accomplished by selecting tubing with a suitable inside diameter and length so as to produce a pressure drop which is in the turbulent flow region. With radioactive systems, a Geiger Tube (not shown), disposed within the tubing coil CO1 (and CO1'), can be used to monitor the gamma activity of the system.

The third section of the system, i.e., the section which is used to measure dissolved gas concentration in water, is connected to the overall system through a further six-port valve V33. This section includes inlets for a calibration gas and for nitrogen ($N_2$), which are connected through a check valve CV32 and a globe valve V34 to one port of six-port valve V33. A thermister TCD32 monitors the temperature of the gas and as discussed below, serves as a reference thermister. A further port of six-port valve V33 is connected to an expansion volume VO1 which is under vacuum pressure (less than about 0.1 Torr) and is bounded by valves V33 and V34, and two further globe valves V41 and V35. Valve V41 is connected to a drain or bottle DR41 and an associated drain tray DT41.

A pressure (vacuum) gauge G31 is connected to the inlet line to volume VO1. Gauge 31, which is preferably a vacuum gauge of the capacitance manometer type, is used to measure the gas and water vapor pressure in the expansion volume VO1. The use of a capacitance manometer vacuum gauge is advantageous in that the measurements provided by gauges of this type are not affected by gas composition.

A thermocouple TCD31 is also connected to the inlet line, and in particular, is located in an area where some water from the sample will collect, i.e., at a low point in the system. This location should be the coldest location in the system in order to produce accurate results. The temperature sensed is used in correcting the value of total pressure sensed by gauge G31. As discussed below, the total gas in the sample is a function of the corrected pressure, expansion volume and the sample volume.

A further pressure gauge G32, also in the form of a capacitance manometer, is used to measure (check) the vacuum pump pressure and the pressures in the system up to valve V35.

Hydrogen gas is measured with a thermo-conductivity detector comprising a thermister bridge formed by reference thermister TCD32 referred to above and a further thermister TCD33. Thermisters (TCD32 and TCD33 are a matched pair of thermisters located in a metal block (not shown). The temperature of thermister TCD33 is that of the nitrogen atmosphere which is atmospheric pressure (760 Torr.). The thermisters TCD32 and TCD33 measure the sum of the product of the partial pressures of each gas and the individual thermoconductivity thereof. The primary purpose of the detector formed by thermisters TCD32 and TCD33 is, as stated, to measure the hydrogen contribution to the gas.

The sample thermister TCD33 is located in the extraction volume VO1 and its temperature measurements are taken at low pressure and compared with pure gas curves. This approach allows measurement of high gas concentrations. Dilution is only with the vapor from the sample and this technique yields lower sensitivities and greater accuracy of the measurement. It is noted that helium gas will interfere to yield higher results and other gases can effect the accuracy of the measurement.

However, at low concentrations these effects are small and at a known concentration the effect can be determined.

A further volume tank VO2 is provided downstream of globe valve V35 to dilute the gases from the sample with nitrogen. This is done in determining the amount of carbon dioxide and some other gases.

A series of valves V36, V37, V38 and V39, are connected as shown between volume tank VO2 and an infrared detector IRD1. A further volume tank VO3, and a vacuum input VAC, and a further gauge G33 are also provided, as illustrated, and the sample, which is diluted with pure nitrogen in volume VO2, and is pressurized to approximately one atmosphere, is inserted in the infrared detector or analyzer IRD1. The detector IRD1 is used to measure one of several possible gases and is selected specifically to measure that gas, i.e., a specific detector is used to measure each specific gas. The analyzer chamber of the infrared detector IRD1 must be evacuated to low pressure prior to insertion of the sample. The quantity of gas is calculated from the concentration factors and the dilution of the sample.

Calibration of the dissolved gas concentration measurement section of the overall system is performed by comparing the pressure readings of the pressure gauges or sensors G31 and G32 at a vacuum less than 1 torr and at atmospheric pressure, using dry nitrogen. The thermister bridge including thermister TCD32 and TCD33 is balanced to read zero. The sample thermister TCD33 is then flooded with dry hydrogen and a curve representing detector output as a function of sample pressure is produced. The carbon dioxide (or other gas) detector portion of this section (including infrared detector IRD1) is calibrated versus carbon dioxide (or other gas) standards. The calibration gas inlet is used to admit mixed gases to system to provide calibration of thermister TCD33 and infrared detector IRD. As discussed above, nitrogen is used to dilute the sample and to serve as the reference gas for the detector formed by thermisters TCD32 and TCD33.

The basic calculations are: (1) total gas = volume constant (total pressure-vapor pressure); and (2) carbon dioxide = volume constant x (i.e., multiplied by) detector reading.

The hydrogen content is calculated as follows: (1) the conductivity of the gas at the detector is a function of the sum of the partial pressures of the gases multiplied by their respective thermal conductivites; (2) the detector zero can be calculated from the atmospheric pressure detector readings of nitrogen and hydrogen and is used at all pressures; (3) most gas conductivities are approximately the same as nitrogen with the exception of hydrogen and helium (and there is no helium in the sample); and, (4) high concentrations of the other gases can be measured or estimated to maintain the accuracy of the hydrogen measurement.

Tests have indicated the accuracy and sensitivity of this section of the overall system to be as follows: Total gas, ±7 cc/Kg in the range of 4 cc/Kg to 400 cc/Kg; hydrogen, ±2 cc/Kg in the range of 2 cc/Kg to 400 cc/Kg; and carbon dioxide, ±4 cc/Kg in the range 4 cc/Kg to 400 cc/Kg.

Figure 2:
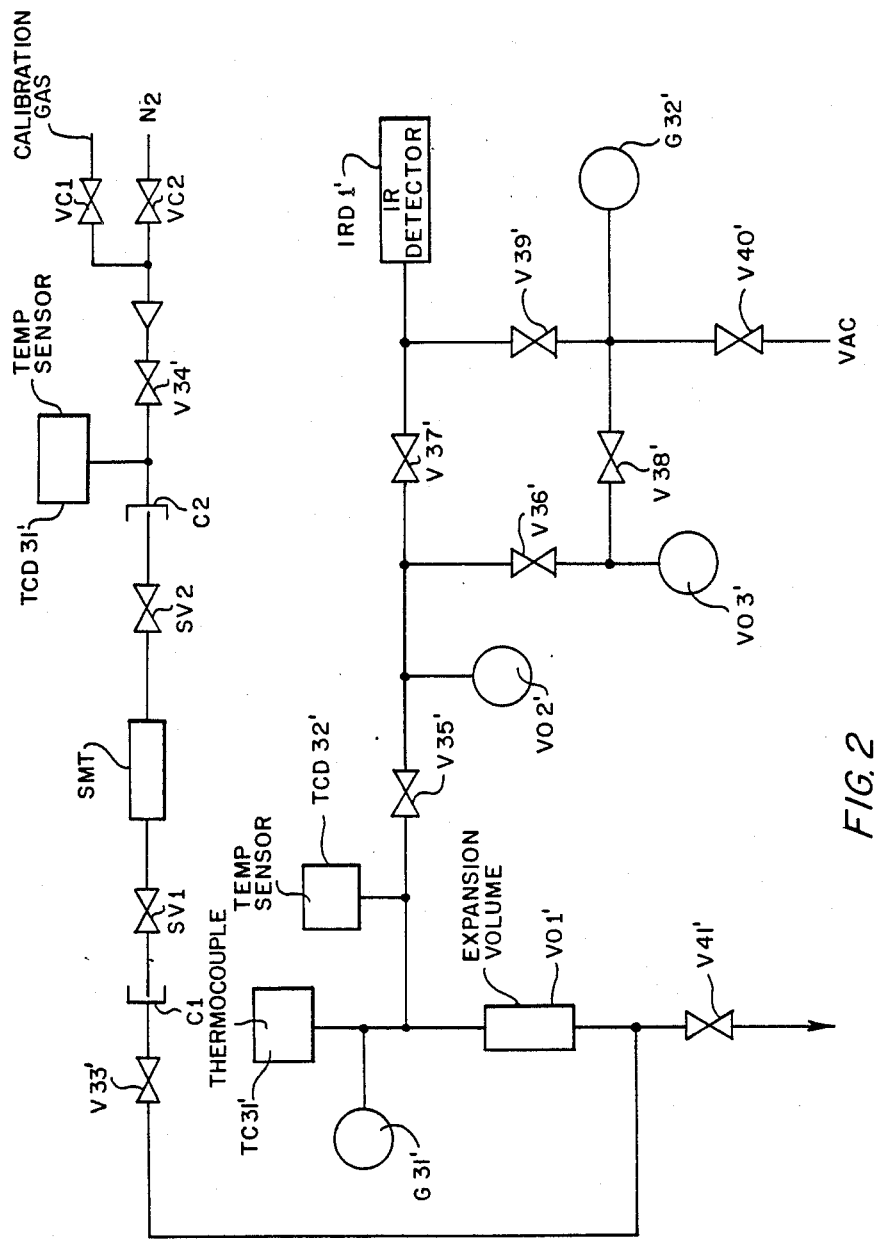
FIG. 2 is a schematic diagram of an alternate embodiment of the dissolved gas measurement section of the unit of FIG. 1.

It will be understood that the gas analysis section has utility apart from the overall system and an independent embodiment is illustrated in FIG. 2. In this embodiment, a sample tube SMT is isolated by sample valves SV1 and SV2 and is connected in the system, by a pair of connectors C1 and C2, to a glove valve V33', corresponding to valve V33 of FIG. 1. The sample tube SMT is advantageously formed by short length of ¼ inch (i.d.) tubing and provides a holding volume for a small amount amount (10 to 15 cc) of sample. The calibration gas and nitrogen inlets are connected through inlet valves VC1 and VC2, respectively (which can also be employed in the system of FIG. 1). Otherwise this embodiment is similar to the corresponding section of FIG. 1 and, accordingly, similar components have been given the same reference numerals with primes attached.

Although the invention has been described relative to exemplary embodiments thereof, it will be understood by those skilled in this art that variations and modifications can be effected in these embodiments without departing from the scope and spirit of the invention.

I claim:

1. Apparatus for measuring dissolved gas concentration in water for gases dissolved in the process stream in a radiological environment, said apparatus comprising:
   means for isolating a small sample of water from the process stream;
   means for extracting the dissolved gases from the sample into a small expansion volume;
   means for measuring the gas pressure of the volume of extracted gas within said expansion volume;
   means for determining the thermoconductivity of the extracted gas within the expansion volume so as to enable the amount of hydrogen in the gas to be determined;
   means for providing dilution of the gases from the sample with an inert gas; and
   infrared detector means for detecting the amount of at least one other gas contained in the extracted gas.

2. Apparatus as claimed in claim 1 wherein said isolating means comprises a short length of small diameter tubing isolated by a pair of valves.

3. Apparatus as claimed in claim 2 wherein said length of tubing is sized to provide a sample of approximately 15 cc.

4. Apparatus as claimed in claim 1 wherein said means for extracting dissolved gases from the sample comprises means defining an expansion volume and a plurality of control valves bounding the expansion volume.

5. Apparatus as claimed in claim 1 wherein said gas pressure measuring means comprising a capacitance monameter.

6. Apparatus as claimed in claim 1 where said thermoconductivity determining means comprises a thermoconductivity detector including first and second thermisters, one of said thermisters being disposed so as to sense the temperature of the extracted gas and the second thermister comprising a reference thermister.

7. Apparatus as claimed in claim 6 wherein said reference thermister is located in a nitrogen atmosphere at atmospheric pressure.

8. Apparatus as claimed in claim 1 wherein said infrared detector means comprises a carbon dioxide detector.

9. Apparatus as claimed in claim 1 further comprising a temperature sensor for sensing the temperature of the water sample to provide correction of the gas pressure measurement.

* * * * *